(12) United States Patent
Bauss et al.

(10) Patent No.: US 7,718,634 B2
(45) Date of Patent: *May 18, 2010

(54) METHOD OF TREATMENT USING BISPHOSPHONIC ACID

(75) Inventors: Frieder Bauss, Neuhofen (DE); Bernhard Pichler, Ketsch (DE); Stephen Turley, Bottmingen (CH)

(73) Assignee: Hoffman-La Roche Inc., Nutley, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 12/139,587

(22) Filed: Jun. 16, 2008

(65) Prior Publication Data

US 2008/0249069 A1    Oct. 9, 2008

Related U.S. Application Data

(63) Continuation of application No. 10/430,007, filed on May 6, 2003, now Pat. No. 7,410,957.

(30) Foreign Application Priority Data

May 10, 2002   (EP)   .................. 02010136

(51) Int. Cl.
A61K 31/675 (2006.01)
(52) U.S. Cl. .................................... 514/108
(58) Field of Classification Search ........ 514/108
See application file for complete search history.

(56) References Cited

U.S. PATENT DOCUMENTS

| | | | |
|---|---|---|---|
| 3,962,432 A | 6/1976 | Schmidt-Dünker | |
| 4,054,598 A | 10/1977 | Blum et al. | |
| 4,267,108 A | 5/1981 | Blum et al. | |
| 4,327,039 A | 4/1982 | Blum et al. | |
| 4,407,761 A | 10/1983 | Blum et al. | |
| 4,621,077 A | 11/1986 | Rosini et al. | |
| 4,624,947 A | 11/1986 | Blum et al. | |
| 4,666,895 A | 5/1987 | Bosies et al. | |
| 4,705,651 A | 11/1987 | Staibano | |
| 4,719,203 A | 1/1988 | Bosies et al. | |
| 4,746,654 A | 5/1988 | Breliere et al. | |
| 4,761,406 A | 8/1988 | Flora et al. | |
| 4,777,163 A | 10/1988 | Bosies et al. | |
| 4,812,311 A | 3/1989 | Uchtman | |
| 4,876,248 A | 10/1989 | Beliere et al. | |
| 4,922,007 A | 5/1990 | Kieczykowski et al. | |
| 4,927,814 A | 5/1990 | Gall et al. | |
| 4,970,335 A | 11/1990 | Isomura et al. | |
| 4,971,958 A | 11/1990 | Bosies et al. | |
| 5,002,937 A | 3/1991 | Bosies et al. | |
| 5,018,651 A | 5/1991 | Hull et al. | |
| 5,019,651 A | 5/1991 | Kieczykowski | |
| 5,206,253 A | 4/1993 | Bosies et al. | |
| 5,344,825 A | 9/1994 | Khanna et al. | |
| 5,356,887 A | 10/1994 | Brenner | |
| 5,358,941 A | 10/1994 | Bechard et al. | |
| 5,431,920 A | 7/1995 | Bechard | |
| 5,462,932 A | 10/1995 | Brenner et al. | |
| 5,488,041 A | 1/1996 | Barbier et al. | |
| 5,622,721 A | 4/1997 | Dansereau et al. | |
| 5,730,715 A | 3/1998 | Sage et al. | |
| 5,882,656 A | 3/1999 | Bechard et al. | |
| 5,965,547 A | 10/1999 | Goodship et al. | |
| 5,994,329 A | 11/1999 | Daifotis et al. | |
| 6,015,801 A | 1/2000 | Daifotis et al. | |
| 6,124,314 A | 9/2000 | Cameron et al. | |
| 6,143,326 A | 11/2000 | Möckel et al. | |
| 6,225,294 B1 | 5/2001 | Daifotis et al. | |
| 6,294,196 B1 | 9/2001 | Gabel et al. | |
| 6,331,533 B1 | 12/2001 | Harvey et al. | |
| 6,333,316 B1 | 12/2001 | Daifotis et al. | |
| 6,419,955 B1 | 7/2002 | Rolf-Dieter et al. | |
| 6,432,932 B1 | 8/2002 | Daifotis et al. | |
| 6,455,514 B2 | 9/2002 | Du Mesnil et al. | |
| 6,468,559 B1 | 10/2002 | Chen et al. | |
| 6,456,443 B2 | 11/2002 | Daifotis et al. | |
| 6,544,967 B2 | 4/2003 | Daifotis et al. | |
| 6,572,874 B1 | 6/2003 | Harrison et al. | |

(Continued)

FOREIGN PATENT DOCUMENTS

CA    2308532    12/2000

(Continued)

OTHER PUBLICATIONS

Quimby et al., J. Org. Chem., 32, pp. 4111-4114 (1967).

(Continued)

*Primary Examiner*—Raymond J Henley, III
(74) *Attorney, Agent, or Firm*—George W. Johnston; Patricia S. Rocha-Tramaloni; David E. Wildman

(57) ABSTRACT

The present invention refers to a pharmaceutical composition of a bisphosphonic acid or salt thereof, and an excipient thereof, and a method of treating disorder characterized by pathologically increased bone resorption comprising orally administering at least 150% of the expected efficious daily dose of a bisphosphonic acid or a pharmaceutically acceptable salt thereof and one or more pharmaceutically acceptable excipients thereof and administering the dose at a period of one two or three consecutive days per month.

10 Claims, No Drawings

U.S. PATENT DOCUMENTS

| | | | |
|---|---|---|---|
| 6,573,252 | B1 | 6/2003 | Del Soldato |
| 6,638,920 | B2 | 10/2003 | Thompson |
| 6,680,307 | B1 | 1/2004 | Bauss et al. |
| 6,692,764 | B2 | 2/2004 | Katdare et al. |
| 6,699,850 | B2 | 3/2004 | Reszka et al. |
| 6,750,213 | B2 | 6/2004 | DiNinno et al. |
| 6,770,289 | B2 | 8/2004 | Uria |
| 6,793,934 | B1 | 9/2004 | Burnside et al. |
| 6,838,584 | B2 | 1/2005 | Blizzard et al. |
| 7,008,640 | B2 | 3/2006 | Watanabe et al. |
| 7,410,957 | B2 * | 8/2008 | Bauss et al. .................. 514/108 |
| 2001/0036936 | A1 | 11/2001 | Day et al. |
| 2001/0051616 | A1 | 12/2001 | Karpf et al. |
| 2002/0006441 | A1 | 1/2002 | Gabel et al. |
| 2003/0118634 | A1 | 6/2003 | Schofield et al. |
| 2003/0139378 | A1 | 7/2003 | Daifotis et al. |
| 2003/0175340 | A1 | 9/2003 | McCallister et al. |
| 2003/0181421 | A1 | 9/2003 | Horowitz et al. |
| 2003/0195171 | A1 | 10/2003 | Daifotis et al. |
| 2003/0225039 | A1 | 12/2003 | Bauss et al. |
| 2004/0087550 | A1 | 5/2004 | Zanetti et al. |
| 2004/0097469 | A1 | 5/2004 | Little et al. |
| 2004/0147484 | A1 | 7/2004 | Boyd et al. |
| 2005/0070504 | A1 | 3/2005 | Burgio, Jr. et al. |
| 2005/0165039 | A1 | 7/2005 | Meissner et al. |

FOREIGN PATENT DOCUMENTS

| | | |
|---|---|---|
| CA | 2149052 | 3/2003 |
| EP | 022 751 | 1/1981 |
| EP | 170 228 | 2/1986 |
| EP | 197 478 | 10/1986 |
| EP | 252 504 | 1/1988 |
| EP | 252 505 | 1/1988 |
| EP | 258 618 | 3/1988 |
| EP | 273 190 | 7/1988 |
| EP | 282 320 | 9/1988 |
| EP | 350 002 | 1/1990 |
| EP | 1 135 140 | 8/2005 |
| GB | 2 153 225 | 8/1985 |
| WO | WO 93/11786 | 6/1993 |
| WO | WO 94/00129 | 1/1994 |
| WO | WO 95/29679 | 11/1995 |
| WO | WO 96/17616 | 6/1996 |
| WO | WO 96/19998 | 7/1996 |
| WO | WO 97/39755 | 10/1997 |
| WO | WO 99/04773 | 2/1999 |
| WO | WO 99/18972 | 4/1999 |
| WO | WO 00/21540 | 4/2000 |
| WO | WO 00/21541 | 4/2000 |
| WO | WO 00/61111 | 10/2000 |
| WO | WO 00/61230 | 10/2000 |
| WO | WO 00/71104 | 11/2000 |
| WO | WO 01/01991 | 1/2001 |
| WO | WO 01/15703 | 3/2001 |
| WO | WO 01/28524 | 4/2001 |
| WO | WO 01/32185 | 5/2001 |
| WO | WO 01/76592 A1 | 10/2001 |
| WO | WO 01/82903 | 11/2001 |
| WO | WO 01/85217 | 11/2001 |
| WO | WO 01/89494 A2 | 11/2001 |
| WO | WO 01/89494 A3 | 11/2001 |
| WO | WO 01/97788 A2 | 12/2001 |
| WO | WO 01/97788 A3 | 12/2001 |
| WO | WO 02/00204 | 1/2002 |
| WO | WO 02/32377 | 4/2002 |
| WO | WO 03/095029 | 11/2003 |
| WO | WO 2004/056373 | 7/2004 |
| WO | WO 2004/067063 | 8/2004 |

OTHER PUBLICATIONS

Riis, B.J., et al., J. of Bone and Mineral Res., (2001) 16(10), pp. 1871-1878.
Delmas, P.D. et al, Calcified Tissue Intern (2003) 72(4), pp. 332.
Chapurlat, R.D., et al, Expert Opinion on Pharmacotherapy, England (2003) 4(3), pp. 391-396.
Hyldstrup et al., Calcified Tissue Int., 53, pp. 297-300 (1993).
Mazess, Lunar News, pp. 1 and 23 (1996).
Mazess, Lunar News, pp. 1 and 31 (1996).
Ringe et al., Rheumatology (Oxford), 42(6):743-9 (2003) (PMID:12730532 Abstract).
Schimmer et al., Clin Ther., 25(1):19-34 (2003) (PMID:12637110 Abstract).
Body et al., Support Care Cancer, 10(5):399-407 (2002) (PMID:12136223 Abstract).
Bergner et al., Nephrol Dial Transplant, 17(7):1281-5 (2002) (PMID:12105253 Abstract).
Body et al., J. Clin. Oncol.,16(12):3890-9 (1998) (PMID:9850035 Abstract).
Merck & Co., NJ, USA, Merck Index 13$^{th}$, 2001, No. 4899.
Pharmaceutical Dosage Forms, 2$^{nd}$ Edition, 1989, vol. 1, pp. 34.
Giron, D., Thermochimica Acta 248-1-59, Elsevier Science B.V., 1995, pp. 1-59.
Goodman & Gilman, Pharmacological Basis of Therapeutics, Ninth Edition, vol. 1, McGraw-Hill, pp. 47,58.
King,R.E., Pharmaceutical Preparations and Their Manufacturing, Farmacia Practica de Remington, VII, pp. 1912-1913.
Giron, D., Journal of Thermal Analysis and Calorimetry, vol. 64, Budapest-2001, pp. 38.
Farmacia Remington, Chapter 76—Preformulation, 17 edition, 1987.
Monier-Faugere t al., J. Bone Miner. Res., 14, pp. 1768-2778 (1999).
Nies, A S., and Spielberg, S.P., Principles of Therapeutics, In Hardman, J.G., and L.E. Limited (Eds.), Goodman & Gilman's the pharmacological bases of therapeutics, ninth edition, pp. 43-62, New York: McGraw-Hill (1996).
Pharmaceutical Dosage Forms, 2$^{nd}$ Edition, 1989, vol. 1, p. 34.
*Therapeutic Dictionary of Washington University*, (1995), pp. 596, Woodley M et al. (only in Cyrillic).
Harris St et al., *Jour. Amer. Med. Assoc.*, (1999) 282(14), pp. 1344-1352.
Watts Nb et al., *Bone*, (1999) 24(1) pp. 65-68.
*Encyclopaedia of Medicaments M.RLS*, (2001) 337, only in Cyrillic.
*Encyclopaedia of Medicaments M.RLS*, (2001) 151, only in Cyrillic.
Seedor et al., *J. Bone Min. Res.*, (1991) 6(4) pp. 339-346.
Bauss et al., *Bone*, (1995) 17, 597, Abstract.
Bauss et al., *J. Bone Min. Res.*, (1996) 11, Suppl 1, 336, M618, Abstract.
Bauss et al., *Osteoporos Int.*, (2004) 15, pp. 423-433, Abstract.
Bell et al., Endocrine, 6, pp. 203-206 (1997).
Berenson et al., Clinical Cancer Research, 7, pp. 478-485 (2001).
Black, D., Twenty-Third Annual Meeting of the ASBMR, 2001.
Filipponi et al., Journal of Bone and Mineral Research, 10, pp. 697-703 (1995).
Fleisch, H., Osteoporosis International, 6, pp. 166-170 (1996).
Krause, C., Chemical Market Reporter, Dec. 17, 2001 at 10.
Mazess, Lunar News 27 (Spring 1999).
Mazess, Lunar News 32 (Winter 2000).
Rosen, C.J., Rev. Endocrine & Metabolic Disorders, 1, pp. 35-43 (2001).
Smith et al., J. Bone and Mineral Research, Abstract A370, p. 402 (1999).
Thiebaud et al., American Journal of Medicine, 103, pp. 298-307 (1997).
Muhlbauer et al., Journal of Bone and Mineral Research, 6, pp. 1003-1011 (1991).
Mazess, Lunar News (Spring 1997).
Kabachnik et al., Russian Chemical Reviews, 43, pp. 733-744 (1974) (Translated from Uspekhi Khimii, 43, 1554-1574 (1974).

Statement of Law and Facts Alleging Obviousness of U.S. Patent 7,192,938 by Generic Pharmaceutical Company.
2003 PDR Monograph for Fosamax®.
2003 PDR Monograph for Actonel®.
2003 PDR Monograph for Skelid®.
Lindsay et al., Osteoporosis International, vol. 13 Suppl. 1, Apr. 2002, Abstract P41SA, p. S16.
Felsenberg et al., Osteoporosis International, vol. 13 Suppl. 1, Apr. 2002, Abstract P42SU, p. S16-S17.
Bonefos®, International prescribing information, Revised Mar. 17, 2006.
Brown et al., Calcif. Tissue Int., 71, pp. 103-111 (2002).
Schnitzer et al., Aging Clin. Exp. Res., 12, pp. 1-12 (2000).
Bauss et al., Journal of Rheumatology, vol. 29, No. 10, pp. 2200-2208 (2002).
Bergner et al., Nephrology Dialysis Transplantation, vol. 170, pp. 1281-1285 (2002).
Bidstrup et al., Bone, vol. 26, No. 3:33S, Supplement (2000), Abstract B23.
Compact Oxford English Dictionary definition of the term 'once'.
Dooley et al., Drugs, vol. 57(1), pp. 101-108 (1999).
Epstein, Current Osteoporosis Reports, vol. 4, pp. 14-20 (2006).
Peterson, "Trends-in-Medicine", American Society for Bone and Mineral Research, San Antonio, Texas at pp. 1-6 (2002).
Recker et al, 26th Annual Meeting of the American Society for Bone and Mineral Research, Abstract F406 (2004).
Rote Liste 2000, Rote Liste® Service GmbH, Frankfurt/Germany, Paragraph 68018 (2000).
Smith, S.Y., Bone, vol. 32, No. 1, pp. 45-55 (2003).
Tanko et al., Bone, vol. 32, pp. 421-426 (2003).
Zeke, Andrew, Declaration of.
Bauss et al., Drugs Fut., 19(1), pp. 13 (1994).
Abstracts from the $5^{th}$ Workshop on Bisphosphonates, Bone, vol. 26, No. 3 Supplement, pp. 27S-42S (2000).
Bone et al., Clinical Therapeutics, 22(1), pp. 15-28 (2000).
Burgio et al., Clinical Pharmacology & Therapeutics, 71(2), at P32, Abstract No. MPI-104 (2002).
Delmas et al., IOF World Congress on Osteoporosis, Lisbon, Portugal, May 10-14; Osteoporosis International, vol. 13, Supplement 1, 2002, published Apr. 2002, p. S15.
Fleisch, Annals in Medicine, 29, 55, pp. 55-62 (1997).
Hochberg et al., Journal of Clinical Endocrinology & Metabolism, 84(4), pp. 1586-1592 (2002).
Kendler et al., Osteoporosis Int., 13 (Suppl. 1), S 32 (Abstract P92SA) (Apr. 2002).
Lalla et al., Journal of Bone and Mineral Research, 11 (Suppl 1), p. S336, Abstract M617 (1996).
Liberman et al., New England Journal of Medicine, 333(22), pp. 1437-1443 (1995).
Ravn et al., Bone, 19/5, pp. 527-533 (1996).
Storm et al., N.E. J. Med., 322, pp. 1265-1271 (1990).
Watts et al., N.E. J. Med., 323, pp. 73-79 (1990).
*Guidelines for preclinical and clinical evaluation of agents used in the prevention of postmenopausal osteoporosis*, Division of Metabolic and Endocrine Drug Products, Food and Drug Admin., (Apr. 1994); available at http://www.fda.gov/cder/guidanceosteo.pdf.
*Guidelines for preclinical evaluation and clinical trials in osteoporosis*, World Health Organization, Geneva (1998).
Etidronate disodium (Didronel) prescribing information.
Electronic Orange Book (http://www.fda.gov/cder/ob/default.htm), listing of tiludronate sodium (Skelid).
Reginster et al., Arthritis and Rheumatism, 35, pp. 967-974 at 973 (1992).
Statement of Law and Facts Alleging Invalidity of U.S. Patent 7,410,957 made by Generic Pharmaceutical Company (#1).
Statement of Law and Facts Alleging Invalidity of U.S. Patent 7,410,957 made by Generic Pharmaceutical Company (#2).
Statement of Law and Facts Alleging Invalidity of U.S. Patent 7,410,957 made by Generic Pharmaceutical Company (#3).
Statement of Law and Facts Alleging Invalidity of U.S. Patent 7,410,957 made by Generic Pharmaceutical Company (#4).
Statement of Law and Facts Alleging Invalidity of U.S. Patent 7,410,957 made by Generic Pharmaceutical Company (#5).
Statement of Law and Facts Alleging Invalidity of U.S. Patent 7,410,957 made by Generic Pharmaceutical Company (#6).
Statement of Law and Facts Alleging Invalidity of U.S. Patent 7,410,957 made by Generic Pharmaceutical Company (#7).
Statement of Law and Facts Alleging Invalidity of U.S. Patent 7,410,957 made by Generic Pharmaceutical Company (#8).
Opposition Brief filed against EP 1506041 B1 by Gedeon Richter Plc.
Opposition Brief filed against EP 1506041 B1 by Generics Ltd.
Opposition Brief filed against EP 1506041 B1 by Laboratories Liconsa, S.A.
Opposition Brief filed against EP 1506041 B1 by Pliva Hrvatska.
Opposition Brief filed against EP 1506041 B1 by Ratiopharm GmbH.
Opposition Brief filed against EP 1506041 B1 by Synthon.
Opposition Brief filed against EP 1506041 B1 by Alfred Tiefenbacher (GmbH & Co. KG).
Opposition Brief filed against EP 1506041 B1 by Teva Pharmaceutical Industries Ltd.
Apotex Answer and Counterclaims filed Oct. 25, 2007 in Case 2:07-cv-04417, United States District Court D.N.J.
Apotex Answer and Counterclaims filed Jan. 12, 2009 in Case 2:08-cv-04053, United States District Court D.N.J.
Cobalt Answer and Counterclaims filed Nov. 28, 2007 in Case 2:07-cv-04540, United States District Court D.N.J.
Last Office Action in U.S. Appl. No. 10/321,208, date mailed Sep. 20, 2006.
Last Office Action in U.S. Appl. No. 10/897,897, date mailed Jul. 26, 2007.
Last Office Action in U.S. Appl. No. 11/390,227, dated mailed Aug. 22, 2007.
Last Office Action in U.S. Appl. No. 11/725,896, date mailed Jan. 25, 2008.
Apotex Alleged Bases of Invalidity of US 7,192,938 from Notice Letter dated Jan. 19, 2009.
Sun Alleged Bases of Invalidity of US 7,192,938 from Notice Letter dated Dec. 12, 2008.
Teva Alleged Bases of Invalidity of US 7,192,938 from Notice Letter dated Aug. 12, 2008.
Thiebaud, D. et al, *Osteoporosis 1996*, Proceedings of the 1996 World Congress on Osteoporosis, International Congress Series, No. 1118, May 1996 p. 321-325.
Hortobagyi, G. N., et al., Efficacy of Pamidronate in Reducing Skeletal Complications in Patients with Breast Cancer and Lytic Bone Metastases, The New England Journal of Medicine (1996) 335:1785-1791.
Ali, S M. et al., Safety and Efficacy of Bisphosphonates Beyond 24 Months in Cancer Patients, Journal of Clinical Oncology (2001), vol. 19, No. 14, pp. 3434-3437.
Mylan Alleged Bases of Invalidity of U.S. Appl. No. 7,192,938 from Notice Letter dated Feb. 23, 2010.
Menssen, H.D. et al, Jour of Clin. Onc, 20:9 (2002)2353-2359 "Effects of Long-Term Intravenous Ibandronate Therapy on Skeletal-Related Events, Survival, and Bone Resorption Markers in Patients with Advanced Multiple Myeloma".
Fleisch, H et al, Endocrine Reviews, 19:1 (1988) 80-100 "Bisphosphonates: Mechanisms of Action".

* cited by examiner

METHOD OF TREATMENT USING BISPHOSPHONIC ACID

PRIORITY TO RELATED APPLICATIONS

This application is a continuation of U.S. application Ser. No. 10/430,007, filed May 6, 2003, now allowed; which claims the benefit of European Application No. 02010136.6, filed May 10, 2002. The entire contents of the above-identified applications are hereby incorporated by reference.

FIELD OF THE INVENTION

The present invention refers to the use of bisphosphonic acids, especially of (1-hydroxy-3-(N-methyl-N-pentyl)aminopropylidene-1,1-bisphosphonic acid (ibandronic acid) or pharmaceutically acceptable salts thereof for the manufacture of pharmaceutical compositions for the prevention or the treatment of disorders characterized by pathologically increased bone resorption, especially for the prevention and treatment of osteoporosis.

BACKGROUND OF THE INVENTION

Bones serve mainly as a support, and consequently bone is frequently regarded as a simple building material. However, bone is a complicated biomaterial adapted to a wide variety of requirements, stimuli and noxae to which it is exposed. Endoprostheses are available as substitutes for bones and joints. However, endoprostheses, even when biomechanically highly refined, do not have an active effect on the environmental and load factors.

A variety of disorders in humans and mammals involve or are associated with abnormal bone resorption. Such disorders include, but are not limited to, osteoporosis, Paget's disease, periprosthetic bone loss or osteolysis, and hypercalcemia of malignancy and metastatic bone disease. The most common of these disorders is osteoporosis, which in its most frequent manifestation occurs in postmenopausal women. Because osteoporosis, as well as other disorders associated with bone loss, are chronic conditions, it is believed that appropriate therapy will generally require chronic treatment.

Bisphosphonates, i.e. bisphosphonic acids or pharmaceutically acceptable salts thereof, are synthetic analogs of the naturally occurring pyrophosphate. Due to their marked affinity for solid-phase calcium phosphate, bisphosphonates bind strongly to bone mineral. Pharmacologically active bisphosphonates are well known in the art and are potent inhibitors of bone resorption and are therefore useful in the treatment and prevention of diseases involving abnormal bone resorption, especially osteoporosis, Paget's disease, hypercalcemia of malignancy, and metastatic and metabolic bone diseases.

Bisphosphonates as pharmaceutical agents are described for example in EP-A-170,228; EP-A-197,478; EP-A-22,751; EP-A-252,504; EP-A-252,505; EP-A-258,618; EP-A-350,002; EP-A-273,190; and WO-A-90/00798, each of which are incorporated herein by reference.

Pharmaceutical forms of currently marketed bisphosphonates are oral formulations (tablets or capsules) or solutions for intravenous injection or infusion. They are systemically well tolerated when administered at therapeutic doses. However, bisphosphonates as a class are irritant to skin and mucous membranes and when given orally on a continuous basis may result in digestive tract side effects, e.g., esophageal adverse events or gastrointestinal disturbances. As a consequence, and due to their low oral bioavailability, the oral route of administration has, to date, had to follow inconvenient recommendations of use for the patient.

Bisphosphonates can be classified into two groups with different modes of action. Ibandronate belongs to the more potent nitrogen-containing bisphosphonates [Russell 1999 Russell R G G, Rogers M J. Bisphosphonates: From the laboratory to the clinic and back again. Bone 25(1):97-106 (1999); Rogers M J, Gordon S, Benford H L, Coxon F P, Luckman S P, Monkkonen J, Frith J C. Cellular Molecular mechanisms of action of bisphosphonates. Cancer 88 (12) Suppl:2961-2978 (2000)]. Ibandronate is one of the most potent bisphosphonates currently under clinical development in osteoporosis and metastatic bone diseases. In animal models of bone resorption, ibandronate is 2, 10, 50 and 500 times more potent than risedronate, alendronate, pamidronate, and clodronate respectively [Mühlbauer R. C., F. Bauss, R. Schenk, M. Janner, E. Bosies, K. Strein, and H. Fleisch. B M 21.0955 a potent new bisphosphonate to inhibit bone resorption. J. Bone Miner. Res. 6: 1003-1011 (1991)].

Ibandronate inhibits bone resorption without any impairment of mineralization (Mühlbauer et al Mühlbauer R. C., F. Bauss, R. Schenk, M. Janner, E. Bosies, K. Strein, and H. Fleisch. BM 21.0955 a potent new bisphosphonate to inhibit bone resorption. J. Bone Miner. Res. 6: 1003-1011 (1991).). It has been shown to decrease osteoclastic activity, thus inhibiting bone destruction. At high doses it also reduces the number of osteoclasts (Mühlbauer et al. Mühlbauer R. C., F. Bauss, R. Schenk, M. Janner, E. Bosies, K. Strein, and H. Fleisch. BM 21.0955 a potent new bisphosphonate to inhibit bone resorption. J. Bone Miner. Res. 6: 1003-1011 (1991)).

As described, bisphosphonates are accepted as providing strong efficacy in the management of osteoporosis. However, given the administration restrictions related to low oral bioavailability and potential for gastro-intestinal effects, there is a clear opportunity for regimens which offer improved convenience and flexibility, leading to a higher level of compliance and superior patient management/satisfaction. Intermitted regimens such as, for example, once weekly administration have been described in the art.

SUMMARY OF THE INVENTION

It has now been found that the prevention or the treatment of disorders characterized by pathologically increased bone resorption such as osteoporosis, can be improved by a monthly administration of 50 to 250 mg of a bisphosphonate or pharmaceutical acceptable salt thereof, especially by a monthly administration of ibandronate, i.e., ibandronic acid or a pharmaceutically acceptable salt thereof.

The present invention is thus concerned with the use of a bisphosphonic acid or a pharmaceutical acceptable salt thereof, especially with the use of ibandronic acid or a pharmaceutical acceptable salt thereof, for the preparation of pharmaceutical compositions for the prevention or the treatment of disorders characterized by pathologically increased bone resorption, wherein the medicament comprises about 50 to 250 mg, preferably about 100 to 150 mg, of a bisphosphonic acid or a acceptable salt thereof, and orally administered in a period of one, two or three consecutive days per month.

Monthly oral treatment by administration of at least 120%, especially of 120% to 200%, of the expected efficacious daily dose offers incremental patient benefits with respect to convenience and compliance as well as superior results. Prior to the completion of the ibandronate clinical development program, no bisphosphonate had prospectively demonstrated fracture reduction efficacy with a drug-free interval beyond daily administration. In summary, it is quite unexpected that fracture reduction benefit can be derived from a monthly administration of an oral bisphosphonate with a single or multiple tablet administration scheme.

Accordingly, the present invention relates to the use of bisphosphonic acids or pharmaceutically acceptable salts, especially ibandronic acid or pharmaceutically acceptable salts thereof for the manufacture of a medicament for the prevention or treatment of disorders characterized by pathologically increased bone resorption, e.g. osteoporosis, wherein the medicament comprises at least 120% of the expected efficacious daily dose of a bisphosphonic acids or acceptable salts thereof and is administered on one, two or three consecutive days per month.

More preferably the invention comprises the use of ibandronic acid or pharmaceutically acceptable salts thereof for the manufacture of a medicament for the prevention or the treatment of disorders characterized by pathologically increased bone resorption wherein the medicament a) comprises about 100 to about 150 mg of ibandronic acid or a pharmaceutically acceptable salt thereof and b) is orally administered in a period of one, two or three consecutive days per month.

DETAILED DESCRIPTION OF THE PREFERRED EMBODIMENT

The term "bisphosphonic acid" means compounds characterized by two phosphonate groups linked by phosphoether bonds to a central (geminal) carbon atom. Such a P—C—P structure is represented by compound I (see, page 6). The use of a specific nomenclature in referring to the bisphosphonate or bisphosphonates is not meant to limit the scope of the present invention, unless specifically indicated.

The term "pharmaceutically acceptable" as used herein means that the salts or chelating agents are acceptable from a toxicity viewpoint.

The term "pharmaceutically acceptable salt" refers to ammonium salts, alkali metal salts such as potassium and sodium (including mono, di- and tri-sodium) salts (which are preferred), alkaline earth metal salts such as calcium and magnesium salts, salts with organic bases such as dicyclohexylamine salts, N-methyl-D-glucamine, and salts with amino acids such as arginine, lysine, and so forth.

The term "disorders characterized by pathologically increased bone resorption" refers to medically defined conditions with or without identifiable cause (such as post-menopausal osteoporosis, idiopathic juvenile osteoporosis, Klinefelter's syndrome; male osteoporosis; osteoporosis due to nutritional factors; organ transplant related osteoporosis; immobilization associated osteoporosis; inflammatory condition and cortico-steroid induced osteoporosis).

The term "one, two or three consecutive days per month" means administration of one to three dose proportional or non-dose proportional tablets on one, two or three consecutive days of the month, preferably on one day per month. As used herein, the term "month" is used in accordance with the generally accepted meaning as a measure of time amounting to approximately four (4) weeks, approximately 30 days, or approximately 1/12 of a calendar year.

The term "medicament" refers to a pharmaceutical composition. The term encompasses single or multiple administration schemes.

Preferably, the medicament is administered on one day per month. Preferably, the medicament is administered as a single dose, however, the scope of the present invention includes pharmaceutical compositions administered as multiple sub-doses such as on two consecutive day per month or on three consecutive days per month.

Preferably, the medicament comprises at least 100%, preferably 120% to 200% of the efficacious dose of bisphosphonic acids or pharmaceutically acceptable salts thereof, more preferably of ibandronic acid or pharmaceutically acceptable salts thereof.

The term "efficacious dose" refers to about 50 to about 250 mg, more preferably to about 100 to about 150 mg, of a bisphosphonate or a pharmaceutically acceptable salt thereof, for example, of ibandronic acid or a pharmaceutically acceptable salt thereof. As noted, the efficacious dose may be a single dose or multiple sub-doses. For example, if the efficacious dose is 150 mg, the dose may be one (1) 150 mg dose, two (2) 75 mg sub-doses administered on one day or on two consecutive days, or three (3) 50 mg sub-doses administered on one day or on two or three consecutive days; if the efficacious dose is 100 mg, the dose may include one (1) 100 mg dose, two (2) 50 mg sub-doses administered on one day or two consecutive days, preferably on two consecutive days.

"Bisphosphonic acids and pharmaceutically acceptable salts thereof" as pharmaceutical agents are described for example in U.S. Pat. Nos. 4,509,612; 4,666,895; 4,719,203; 4,777,163; 5,002,937 and 4,971,958 and in European Patent Applications Nos. 252,504 and 252,505, herein incorporated by reference for such description.

Methods for the preparation of bisphosphonic acids and pharmaceutically acceptable salts thereof may be found in, e.g., U.S. Pat. Nos. 3,962,432; 4,054,598; 4,267,108; 4,327,039; 4,407,761; 4,621,077; 4,624,947; 4,746,654; 4,970,335; 5,019,651; 4,761,406; 4,876,248; in J. Org. Chem. 32, 4111 (1967) and European Patent Application 252,504, herein incorporated by reference. The pharmaceutically acceptable salts of bisphosphonic acids may also be employed in the instant invention. Examples of base salts of bisphosphonic acids include ammonium salts, alkali metal salts such as potassium and sodium (including mono, di- and tri-sodium) salts (which are preferred), alkaline earth metal salts such as calcium and magnesium salts, salts with organic bases such as dicyclohexylamine salts, N-methyl-D-glucamine, and salts with amino acids such as arginine, lysine, and so forth. Nontoxic, physiologically acceptable salts are preferred. The salts may be prepared by methods known in the art, such as described in European Patent Application 252,504 or in U.S. Pat. No. 4,922,077, incorporated herein by reference.

In this invention, the medicament comprises 100 to 150 mg of a ibandronic acid or a pharmaceutically acceptable salt thereof. The pharmaceutical composition comprises at least 150% of a bisphosphonic acid or a pharmaceutically acceptable salt thereof, and one or more pharmaceutically acceptable excipients thereof. In one embodiment, the bisphosphonic acid is ibandronic acid. Preferably, the medicament is administered as a single dose.

In a preferred embodiment of the present invention, the term "bisphosphonate" of the present invention corresponds to compounds of general formula

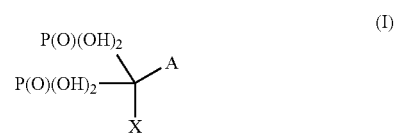

wherein A and X are independently selected from the group consisting of hydrogen, hydroxy, halogen, amino, SH, phenyl, alkyl, mono- or dialkylamino, mono- or dialkylaminoalkyl, alkoxy, thioalkyl, thiophenyl, and aryl or heteroaryl moieties selected from the group consisting of phenyl, pyridyl, furanyl, pyrrolidinyl, imidazolyl, and benzyl, wherein the aryl or heteroaryl moiety is optionally substituted with alkyl.

In the foregoing chemical formula, A can include X, and X include A such that the two moieties can form part of the same cyclic structure.

The foregoing chemical formula is also intended to encompass carbocyclic, aromatic and heteroaromatic structures for the A and/or X substituents, e.g. naphthyl, quinolyl, isoquinolyl, adamantyl, and chlorophenylthio.

Preferred structures are those in which A is selected from the group consisting of hydrogen, hydroxy, and halogen, an X is selected from the group consisting of alkyl, halogen, thiophenyl, thioalkyl and dialkylaminoalkyl.

More preferred structures are those in which A is selected from the group consisting of hydrogen, hydroxy, and Cl and X is selected from the group consisting of alkyl, Cl, chlorophenylthio and dialkylaminoalkyl.

The preferred bisphosphonic acid or pharmaceutically acceptable salt is selected from the group consisting of alendronate, cimadronate, clodronate, tiludronate, etidronate, ibandronate, incadronate, minodronate, neridronate, olpadronate, risedronate, pamidronate, piridronate, zolendronate, EB-1053 or acceptable salts thereof, e.g., ibandronic acid, monosodium salt, monohydrate.

Ibandronic acid (1-hydroxy-3-(N-methyl-N-pentyl)aminopropylidene-1,1-bisphosphonic acid) or physiologically compatible salts thereof are particularly preferred, e.g., ibandronic acid, monosodium salt, monohydrate.

The bisphosphonates and pharmaceutically acceptable salts may be administered alone or in combination with other bone active drugs, either in fixed combinations or separately both physically and in time, including hormones, such as a steroid hormone, e.g., an estrogen; a partial estrogen agonist, or estrogen-gestagen combination; a calcitonin or analogue or derivative thereof, e.g., salmon, eel or human calcitonin parathyroid hormone or analogues thereof, e.g., PTH (1-84), PTH (1-34), PTH (1-36), PTH (1-38), PTH (1-31)NH2 or PPTS 893; a SERM (Selective Estrogen Receptor Modulator), e.g., raloxifene, lasofoxifene, TSE-434, FC1271, tibolone, vitamin D or an analog. Such additional bone active drugs may be administered more frequently than the bisphosphonate.

Appropriate pharmaceutical compositions are known in the art and have been described e.g., in U.S. Pat. Nos. 6,143,326 and 6,294,196, herein incorporated by reference.

For the preparation of tablets, coated tablets, dragees or hard gelatine capsules, the compounds of the present invention may be admixed with pharmaceutically inert, inorganic or organic excipients. Examples of suitable excipients for tablets, dragees or hard gelatine capsules include lactose, maize starch or derivatives thereof, talc or stearic acid or salts thereof.

The pharmaceutical compositions may also contain preserving agents, solubilizing agents, stabilizing agents, wetting agents, emulsifiers, sweeteners, colorants, odorants, salts for the variation of osmotic pressure, buffers, coating agents or antioxidants. They may also contain other therapeutically valuable agents. Preferably, the pharmaceutical composition is a film coated tablet wherein the tablet core comprises 50 to 200 mg of a bisphosphonic acid or a pharmaceutically acceptable salt thereof as defined above and one or more pharmaceutically acceptable excipients selected from the group consisting of lactose, polyvinylpyrrolidone, microcrystalline cellulose, crospovidone, stearic acid, silicon dioxide and the tablet core comprises one or more pharmaceutically acceptable excipients selected from the group consisting of hydroxypropyl methylcellulose, titanium dioxide, talc and polyethylene glycol 6000. These compositions are known in the art and described for example in U.S. Pat. Nos. 6,143,326 and 6,294,196.

Another aspect of the present invention is a method for treating, reducing or preventing disorders characterized by pathologically increased bone resorption comprising to a mammal administration of an effective amount of bisphosphonic acids or acceptable salts thereof. In particular, the invention refers to a method for treating, reducing or preventing disorders characterized by pathologically increased bone resorption comprising oral administration of an effective amount of a bisphosphonic acid or a pharmaceutically acceptable salt thereof, wherein approximately 50 to 250 mg bisphosphonic acid or a pharmaceutically acceptable salt thereof are administered on one, two or three consecutive days per month. As noted above, the effective amount of bisphosphonic acid or pharmaceutically acceptable salt thereof may be administered as a single dose or as multiple sub-doses.

Preferably, in the method comprises administration of about 50 to 250 mg, preferably about 100 to 150 mg, of a bisphosphonate or a pharmaceutically acceptable salt thereof on one, two or three consecutive days per month. While the method includes administration of the dose through multiple sub-dosing, the preferred method provides a single dose. Examples for administration of the dose through multiple sub-dosing are as follows, if the efficacious dose is 150 mg, the dose may be two (2) 75 mg sub-doses administered on one day or on two consecutive days, or three (3) 50 mg sub-doses administered on one day or on two or three consecutive days; if the efficacious dose is 100 mg, the dose may be two (2) 50 mg sub-doses administered on one day or two consecutive days, preferably on two consecutive days. The preferred bisphosphonate is ibandronate or a pharmaceutically acceptable salt thereof, e.g., ibandronic acid, monosodium salt, monohydrate.

Preferably, in the method according to the present invention, the bisphosphonic acid is selected from the group consisting of alendronate, cimadronate, clodronate, tiludronate, etidronate, ibandronate, incadronate, minodronate, neridronate, olpadronate, risedronate, pamidronate, piridronate, zolendronate, EB-1053 or pharmaceutical acceptable salts thereof. More preferably, the bisphosphonic acid is ibandronate or a pharmaceutically acceptable salt thereof, e.g. ibandronic acid, monosodium salt, monohydrate.

The invention will now be explained with reference to exemplified embodiments.

EXAMPLES

Example 1

Pharmaceutical Composition

The Example shows the composition of a 50 mg tablet. The composition and preparation of these tablets is known in the art and described for example in U.S. Pat. Nos. 6,143,326 and 6,294,196.

Other compositions may be prepared by adjusting the ingredients according to the amount of bisphosphonate, e.g. ibandronic acid, monosodium salt, monohydrate.

| 50 mg film-coated tablet | |
|---|---|
| Components | mg per tablet |
| Tablet core: | |
| Ibandronic acid, monosodium salt, monohydrate | 56.250 |
| Lactose monohydrate | 92.750 |
| Povidone K 25 | 5.000 |
| Microcrystalline cellulose | 30.000 |
| Crospovidone | 10.000 |
| Purified stearic acid | 4.000 |
| Colloidal silicon dioxide | 2.000 |
| Tablet coat: | |
| Hydroxypropyl methylcellulose | 5.1425 |
| Titanium dioxide | 2.4650 |
| Talc | 0.8925 |
| Polyethylene glycol 6,000 | 1.5000 |
| Final weight: | 210.000 |

What is claimed is:

1. A method for treating or inhibiting postmenopausal osteoporosis in a postmenopausal woman in need of treatment or inhibition of postmenopausal osteoporosis by administration of a pharmaceutically acceptable salt of ibandronic acid, comprising:
   (a) commencing the administration of the pharmaceutically acceptable salt of ibandronic acid by orally administering to the postmenopausal woman, on a single day, a first dose in the form of a tablet, wherein the tablet comprises an amount of the pharmaceutically acceptable salt of ibandronic acid that is equivalent to about 150 mg of ibandronic acid; and
   (b) continuing the administration by orally administering, once monthly on a single day, a tablet comprising an amount of the pharmaceutically acceptable salt of ibandronic acid that is equivalent to about 150 mg of ibandronic acid.

2. The method of claim 1, wherein the pharmaceutically acceptable salt is a sodium salt of ibandronic acid.

3. The method of claim 2 wherein the pharmaceutically acceptable sodium salt is a monosodium salt of ibandronic acid.

4. The method of claim 3 wherein the pharmaceutically acceptable monosodium salt of ibandronic acid is a monohydrate.

5. A method for treating or inhibiting postmenopausal osteoporosis in a postmenopausal woman in need of treatment or inhibition of postmenopausal osteoporosis by administration of a pharmaceutically acceptable salt of ibandronic acid, consisting essentially of orally administering to the postmenopausal woman, once monthly on a single day, a tablet comprising an amount of the pharmaceutically acceptable salt of ibandronic acid that is equivalent to about 150 mg of ibandronic acid.

6. The method of claim 5, wherein the pharmaceutically acceptable salt is a sodium salt of ibandronic acid.

7. The method of claim 6 wherein the pharmaceutically acceptable sodium salt is a monosodium salt of ibandronic acid.

8. The method of claim 7 wherein the pharmaceutically acceptable monosodium salt of ibandronic acid is a monohydrate.

9. A method for treating or inhibiting postmenopausal osteoporosis in a postmenopausal woman in need of treatment or inhibition of postmenopausal osteoporosis by administration of a pharmaceutically acceptable salt of risedronic acid, comprising:
   (a) commencing the administration of the pharmaceutically acceptable salt of risedronic acid by orally administering to the postmenopausal woman, on a single day, a first dose in the form of a tablet, wherein the tablet comprises an amount of the pharmaceutically acceptable salt of risedronic acid that is equivalent to about 150 mg of risedronic acid; and
   (b) continuing the administration by orally administering, once monthly on a single day, a tablet comprising an amount of the pharmaceutically acceptable salt of risedronic acid that is equivalent to about 150 mg of risedronic acid.

10. A method for treating or inhibiting postmenopausal osteoporosis in a postmenopausal woman in need of treatment or inhibition of postmenopausal osteoporosis by administration of a pharmaceutically acceptable salt of risedronic acid, consisting essentially of orally administering to the postmenopausal woman, once monthly on a single day, a tablet comprising an amount of the pharmaceutically acceptable salt of risedronic acid that is equivalent to about 150 mg of risedronic acid.

\* \* \* \* \*